United States Patent [19]

DiPalma et al.

[11] Patent Number: 5,545,156
[45] Date of Patent: Aug. 13, 1996

[54] ABSORBENT ARTICLE HAVING A PREFORMED MEMBER

[75] Inventors: Joseph DiPalma, Neenah; Sowmya S. Anjur, Appleton, both of Wis.

[73] Assignee: Kimberly-Clark Corporation, Neenah, Wis.

[21] Appl. No.: 362,705

[22] Filed: Dec. 22, 1994

[51] Int. Cl.$^6$ ........................................................ A61F 13/15
[52] U.S. Cl. ..................... 604/385.1; 604/378; 604/387
[58] Field of Search ............................... 604/385.1, 378, 604/386, 387

[56] References Cited

U.S. PATENT DOCUMENTS

| | | | |
|---|---|---|---|
| Re. 33,351 | 9/1990 | Papajohn | 604/387 |
| 907,784 | 12/1908 | Green . | |
| 1,192,439 | 7/1916 | Luellen . | |
| 1,946,626 | 2/1934 | Jurgensen | 128/290 |
| 2,043,325 | 6/1936 | Jackson, Jr. | 128/284 |
| 2,064,431 | 12/1936 | Jurgensen | 128/290 |
| 2,092,346 | 9/1937 | Arone | 128/284 |
| 2,331,355 | 10/1943 | Strongson | 128/290 |
| 2,566,451 | 9/1951 | Julien | 128/290 |
| 2,683,457 | 7/1954 | Cunningham | 128/290 |
| 2,747,575 | 5/1956 | Mercer | 128/290 |
| 2,973,760 | 3/1961 | Dudley | 128/287 |
| 3,092,109 | 6/1963 | Mosier | 128/289 |
| 3,121,427 | 2/1964 | Mosier | 128/284 |
| 3,183,909 | 5/1965 | Roehr | 128/290 |
| 3,262,451 | 7/1966 | Morse | 128/290 |
| 3,444,859 | 5/1969 | Kalwaites | 128/284 |
| 3,572,342 | 3/1971 | Lindquist et al. | 128/287 |
| 3,575,174 | 4/1971 | Mogor | 128/290 |
| 3,595,235 | 7/1971 | Jespersen | 128/284 |
| 3,687,350 | 8/1972 | Warburton | 229/2.5 |
| 3,769,979 | 11/1973 | Freney | 128/290 R |
| 3,805,790 | 4/1974 | Kaczmarzyk et al. | 128/290 R |
| 3,844,288 | 10/1974 | Kiela | 128/287 |
| 3,857,394 | 12/1974 | Alemany | 128/260 |
| 3,865,112 | 2/1975 | Roeder | 128/290 R |
| 3,888,254 | 6/1975 | Hendricks | 129/290 R |
| 4,031,897 | 6/1977 | Graetz | 128/286 |
| 4,046,147 | 9/1977 | Berg | 128/290 R |
| 4,059,114 | 11/1977 | Richards | 128/287 |
| 4,079,739 | 3/1978 | Whitehead | 128/290 R |
| 4,184,498 | 1/1980 | Franco | 128/290 R |
| 4,324,246 | 4/1982 | Mullane et al. | 128/287 |
| 4,340,058 | 7/1982 | Pierce et al. | 128/287 |

(List continued on next page.)

FOREIGN PATENT DOCUMENTS

| | | |
|---|---|---|
| 0256871A2 | 2/1988 | European Pat. Off. . |
| 0400694A1 | 12/1990 | European Pat. Off. . |
| 0534488A1 | 3/1993 | European Pat. Off. . |
| 0597273A1 | 5/1994 | European Pat. Off. . |
| 0607985A1 | 7/1994 | European Pat. Off. . |
| 0626158A1 | 11/1994 | European Pat. Off. . |
| WO93/01782 | 2/1993 | WIPO . |
| WO93/12745 | 7/1993 | WIPO . |
| WO93/19711 | 10/1993 | WIPO . |
| WO94/16658 | 8/1994 | WIPO . |
| WO94/27538 | 12/1994 | WIPO . |

OTHER PUBLICATIONS

Copending patent application U.S. Ser. No. 08/058,249 filed May 12, 1993 entitled "ABSORBENT ARTICLE." (K–C Docket No. 10,849).

Copending patent application U.S. Ser. No. 08/263,178 filed Jun. 21, 1994 entitled "ABSORBENT ARTICLE HAVING ENHANCED WICKING CAPACITY." (K–C Docket No. 10,912.1).

*Primary Examiner*—Michael J. Milano
*Attorney, Agent, or Firm*—Mark L. Davis

[57] ABSTRACT

An absorbent article with an outer perimeter is disclosed having a cover, a liquid-impermeable preformed member and an absorbent core positioned therebetween. The preformed member has bulge for close body contact between the wearer and the absorbent article and a barrier means for intercepting body fluid migrating from the absorbent core toward the outer perimeter of the sanitary napkin. The bulge extends above the bodyfacing surface of the absorbent core while the barrier means encircles the absorbent core and extends above the periphery of the absorbent core.

23 Claims, 2 Drawing Sheets

U.S. PATENT DOCUMENTS

| | | | |
|---|---|---|---|
| 4,342,314 | 8/1982 | Radel et al. | 128/287 |
| 4,433,972 | 2/1984 | Malfitano | 604/385 |
| 4,458,468 | 7/1984 | Sivilich | 53/428 |
| 4,463,045 | 7/1984 | Ahr et al. | 428/131 |
| 4,490,147 | 12/1984 | Pierce et al. | 604/378 |
| 4,501,586 | 2/1985 | Holtman | 604/380 |
| 4,526,825 | 7/1985 | Whitehead | 428/74 |
| 4,554,191 | 11/1985 | Korpman | 428/35 |
| 4,559,051 | 12/1985 | Hanson | 604/385 R |
| 4,579,556 | 4/1986 | McFarland | 604/385 A |
| 4,624,666 | 11/1986 | DeRossett et al. | 604/366 |
| 4,631,062 | 12/1986 | Lassen et al. | 604/385 R |
| 4,648,876 | 3/1987 | Becker et al. | 604/370 R |
| 4,655,759 | 4/1987 | Romans-Hess et al. | 604/385 R |
| 4,657,538 | 4/1987 | Becker et al. | 604/381 |
| 4,673,403 | 6/1987 | Lassen et al. | 604/385 R |
| 4,677,810 | 7/1987 | Spano | 53/428 |
| 4,681,577 | 7/1987 | Stern et al. | 604/378 |
| 4,681,578 | 7/1987 | Anderson et al. | 604/385 R |
| 4,681,793 | 7/1987 | Linman et al. | 428/138 |
| 4,685,914 | 8/1987 | Holtman | 604/368 |
| 4,690,679 | 9/1987 | Mattingly, III et al. | 604/383 |
| 4,692,160 | 9/1987 | Nussbaumer | 604/331 |
| 4,699,823 | 10/1987 | Kellenberger et al. | 428/219 |
| 4,701,177 | 10/1987 | Ellis et al. | 604/385 A |
| 4,710,185 | 12/1987 | Sneyd, Jr. et al. | 604/372 |
| 4,710,186 | 12/1987 | DeRossett et al. | 604/383 |
| 4,728,381 | 3/1988 | Jezuit et al. | 156/245 |
| 4,730,761 | 3/1988 | Spano | 225/2 |
| 4,731,065 | 3/1988 | Yamada | 604/355 |
| 4,740,342 | 4/1988 | Menard et al. | 264/549 |
| 4,752,349 | 6/1988 | Gebel | 156/267 |
| 4,753,644 | 6/1988 | Cottenden et al. | 604/378 |
| 4,755,413 | 7/1988 | Morris | 428/138 |
| 4,758,240 | 7/1988 | Glassman | 604/379 |
| 4,770,657 | 9/1988 | Ellis et al. | 604/385 A |
| 4,772,282 | 9/1988 | Oakley | 604/385.1 |
| 4,778,372 | 10/1988 | Mutti et al. | 425/294 |
| 4,781,710 | 11/1988 | Megison et al. | 604/378 |
| 4,781,713 | 11/1988 | Welch et al. | 604/385.1 |
| 4,795,454 | 1/1989 | Dragoo | 604/385.2 |
| 4,795,455 | 1/1989 | Luceri et al. | 604/386 |
| 4,798,603 | 1/1989 | Meyer et al. | 604/378 |
| 4,798,638 | 1/1989 | Marbach | 156/69 |
| 4,804,380 | 2/1989 | Lassen et al. | 604/385.1 |
| 4,808,177 | 2/1989 | DesMarais et al. | 604/385.1 |
| 4,814,123 | 3/1989 | Hautemont | 264/40.6 |
| 4,820,295 | 4/1989 | Chapas et al. | 604/385.1 |
| 4,822,332 | 4/1989 | Kajander | 604/16 |
| 4,828,555 | 5/1989 | Hermansson | 604/379 |
| 4,846,824 | 7/1989 | Lassen et al. | 604/385.1 |
| 4,865,597 | 9/1989 | Mason, Jr. et al. | 604/385.1 |
| 4,872,870 | 10/1989 | Jackson | 604/366 |
| 4,886,513 | 12/1989 | Mason, Jr. et al. | 604/385.1 |
| 4,897,084 | 1/1990 | Ternstrom et al. | 604/385.2 |
| 4,908,026 | 3/1990 | Sukiennik et al. | 604/378 |
| 4,936,839 | 6/1990 | Molee et al. | 604/378 |
| 4,944,735 | 7/1990 | Mokry | 604/385.2 |
| 4,950,262 | 8/1990 | Takagi | 604/385.1 |
| 4,988,344 | 1/1991 | Reising et al. | 604/368 |
| 4,988,345 | 1/1991 | Reising | 604/368 |
| 5,013,309 | 5/1991 | Baigas, Jr. et al. | 604/368 |
| 5,021,051 | 6/1991 | Hiuke | 604/385.2 |
| 5,026,364 | 6/1991 | Robertson | 604/385.1 |
| 5,030,229 | 7/1991 | Yang | 604/385.1 |
| 5,032,121 | 7/1991 | Mokry | 604/385.2 |
| 5,037,409 | 8/1991 | Chen et al. | 604/358 |
| 5,053,029 | 10/1991 | Yang | 604/385.1 |
| 5,064,489 | 11/1991 | Ujimoto et al. | 156/164 |
| 5,074,855 | 12/1991 | Rosenbluth et al. | 604/385.1 |
| 5,074,856 | 12/1991 | Coe et al. | 604/385.1 |
| 5,092,860 | 3/1992 | Pigneul | 604/380 |
| 5,098,422 | 3/1992 | Davis et al. | 604/385.1 |
| 5,104,396 | 4/1992 | Oatley et al. | 604/379 |
| 5,129,893 | 7/1992 | Thoren | 604/385.2 |
| 5,134,007 | 7/1992 | Reising et al. | 427/78 |
| 5,135,521 | 8/1992 | Luceri et al. | 604/383 |
| 5,147,343 | 9/1992 | Kellenberger | 604/368 |
| 5,171,302 | 12/1992 | Buell | 604/385.1 |
| 5,178,139 | 1/1993 | Angelillo | 128/403 |
| 5,181,563 | 1/1993 | Amaral | 604/385.2 |
| 5,197,959 | 3/1993 | Buell | 604/385.1 |
| 5,207,662 | 5/1993 | James | 604/385.2 |
| 5,211,641 | 5/1993 | Roos et al. | 604/385.1 |
| 5,219,341 | 6/1993 | Serbiak et al. | 604/361 |
| 5,234,422 | 8/1993 | Sneller et al. | 604/385.2 |
| 5,248,309 | 9/1993 | Serbiak et al. | 604/368 |
| 5,267,992 | 12/1993 | Van Tilburg | 604/387 |
| 5,275,591 | 1/1994 | Mavinkurve | 604/387 |
| 5,281,208 | 1/1994 | Thompson et al. | 604/378 |
| 5,324,278 | 6/1994 | Visscher et al. | 604/385.1 |
| 5,382,245 | 1/1995 | Thompson et al. | 604/367 |

ABSORBENT ARTICLE HAVING A PREFORMED MEMBER

FIELD OF THE INVENTION

This invention relates generally to disposable absorbent articles for absorbing body fluid and in particular to thin sanitary napkins for absorbing menstrual fluid. More particularly, the present invention relates to sanitary napkins having a flexible preformed member with a central absorbent hump for close body contact and barrier means for intercepting fluid migration.

BACKGROUND OF THE INVENTION

All manner and variety of absorbent devices or appliances have been configured for the absorption of body fluids, such as menses, and are well known. Such devices are expected to absorb the body fluid, retain the fluid within the absorbent and to prevent the discharged body fluids from soiling the person and/or clothing.

In the formation of such disposable absorbent devices they commonly include a liquid-permeable, bodyfacing cover, an absorbent core and a liquid-impermeable backing sheet or baffle. These absorbent devices, whether utilized as diapers, incontinence garments or sanitary napkins are subject to failure. Leakage from absorbent devices is generally attributed to a high concentration of fluid absorption at the point of fluid insult. At this point the absorbent material in the device becomes super-saturated and unable to accept, to a large degree, additional fluids from the body. Using a sanitary napkin as an example, the menses will generally migrate radially from the point of insult and will leak from the sides. This usually results in the soiling of wearer, typically around the thigh region, and the undergarment. In the area of sanitary napkins, it has been suggested that at least 20–25 percent of all sanitary napkins experience side leakage. This incidence of leakage increases for those sanitary napkins having increased absorbency designed primarily for medium to heavy flow.

To overcome the problem of side leakage, sanitary napkins have been constructed having elasticized sides that urge the sides upward or cause the sanitary napkin to form a cup shape.

Another method of preventing side leakage has been to extend wings, flaps or panels (hereinafter wings) from the edges of the sanitary napkin. The wings generally extend over the edges of the undergarment and adhere to the underside of the crotch portion or to themselves. The wings typically assist the garment adhesive, if present, to hold the sanitary napkin in position during use. However, it is possible that these elasticized edges or wings will fold inward, partially occluding the cover surface and thereby diminishing the efficacy of the sanitary napkin. In some cases this folding results in the edges actually contributing to incidence of failure.

Improving the performance of sanitary napkins continues to be a formidable undertaking, although a number of improvements have been made in both materials and construction. However, eliminating leakage, particularly along the inside of the thighs without compromising comfort and fit has not met the desired needs of the consumer.

Therefore, there remains a need for a sanitary napkin that will be comfortable to wear while decreasing the chance of side leakage associated with the use of sanitary napkins during the menstrual period.

SUMMARY OF THE INVENTION

Briefly, this invention relates to disposable absorbent articles, and more particularly to sanitary napkins which are designed to absorb body fluids, such as menstrual fluid, and other excrements discharged by the body during a menstrual period. The present invention provides for an absorbent article having close body contact and improved side leakage protection. Although described hereafter as a sanitary napkin, it is understood that the invention can be adapted for use in disposable diapers, adult incontinence devices, training pants and the like where absorption of at least 8 grams of fluid is desired.

The sanitary napkin generally includes a liquid-permeable cover, a liquid-impermeable preformed member and an absorbent core located between the cover and the preformed member. The preformed member has a bulge and a barrier. The bulge has an apex that extends above a bodyfacing surface of the absorbent core. In a preferred embodiment, the bulge is longitudinally oriented and more preferably, longitudinally oriented and medially positioned. The barrier encircles the periphery of the absorbent core and is adapted for intercepting fluid migrating toward a perimeter of the sanitary napkin.

In another preferred embodiment of this invention, the sanitary napkin includes a liquid-permeable cover, a liquid-impermeable preformed member, an absorbent core located between the cover and the preformed member and a baffle secured to the garment-facing surface of the preformed member. The preformed member has a bulge with an apex that extends above the bodyfacing surface of the absorbent core and a barrier encircling the periphery of the absorbent core. The barrier is adapted for intercepting fluid migrating toward the perimeter of the sanitary napkin. The bulge and baffle cooperate to form a pocket. Advantageously, the pocket preferentially maintains the bulge oriented toward the body of the wearer when lateral forces are exerted on the sanitary napkin during use. This construction provides a sanitary napkin having improved body conforming characteristics.

Another preferred embodiment of this invention provides for a sanitary napkin having a liquid-permeable cover, a liquid-impermeable preformed member, a first absorbent core located between the cover and the preformed member and a baffle secured to the garment-facing surface of the preformed member. The preformed member has a bulge with an apex that extends above the bodyfacing surface of the absorbent core and a barrier encircling the periphery of the absorbent core. The barrier is adapted for intercepting fluid migrating toward the perimeter of the sanitary napkin. The barrier has first and second spaced apart walls. The baffle and preformed member are coextensive and form first and second pockets between the barrier walls and the baffle and the second pocket is the area between the bulge and the baffle. The first pocket contains a second absorbent core and the second pocket contains a third absorbent core. The first absorbent core is in liquid communication with the second and third absorbent cores via one or more apertures in the preformed member proximate the first absorbent core.

It is a general object of this invention to provide an absorbent article exhibiting improved body contact as well as improved side leakage protection. A more specific object of the invention is to provide an improved sanitary napkin having improved body contacting and body conforming components to improve the overall efficacy of the sanitary napkin.

Another object of this invention is to provide a sanitary napkin having a preformed member that provides intimate contact to the wearer's body, improved side leakage prevention and is comfortable to wear. Another object of this invention is to provide a sanitary napkin having a longitudinally oriented bulge for improved body contact and a barrier for intercepting body fluid migrating toward the outer perimeter of the sanitary napkin.

These and other objects, features and advantages are readily apparent when considered in reference to the following specification and the accompanying drawings, wherein there are illustrated and described sanitary napkins showing preferred embodiments of the present invention. It is to be understood that the inventive concept is not to be considered limited to the constructions disclosed except as determined by the scope of the appended claims.

DETAILED DESCRIPTION OF THE PREFERRED EMBODIMENTS

Figure 1:
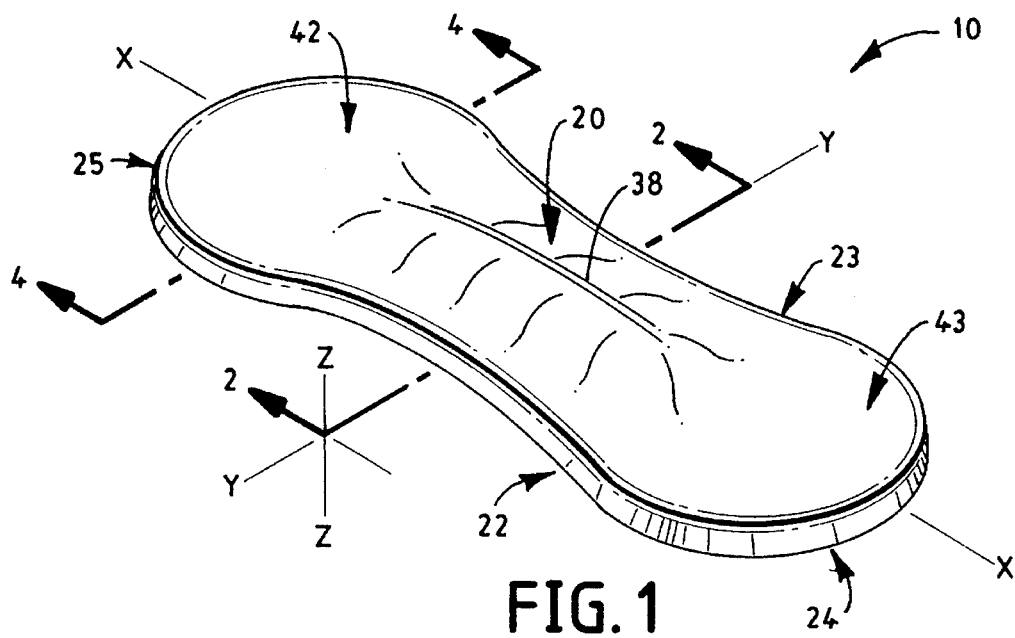
FIG. 1 is a perspective view of an embodiment of this invention illustrated as a sanitary napkin.

Referring to the drawings, a disposable absorbent article 10 of the present invention is illustrated in the form of a sanitary napkin. Typically, a sanitary napkin is worn by a female to absorb body fluids, such as menses, blood, urine and other body excrements discharged during a menstrual period. Although the present invention will be described with reference to a sanitary napkin those skilled in the art will realize that such description is meant to be exemplary only and should not be deemed as limiting the scope of the present invention. The present invention will now be described in greater detail with reference to the Figures.

Figure 2:
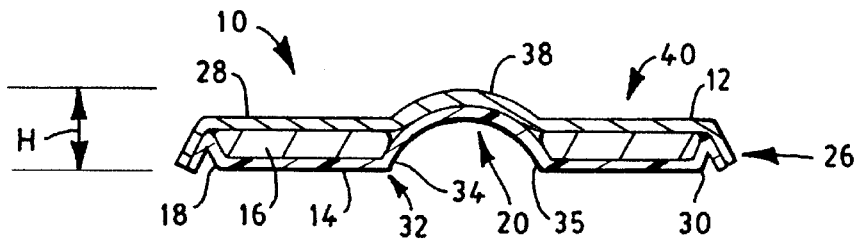
FIG. 2 is a cross-sectional view of the sanitary napkin taken along line 2—2 of FIG. 1
Figure 3:
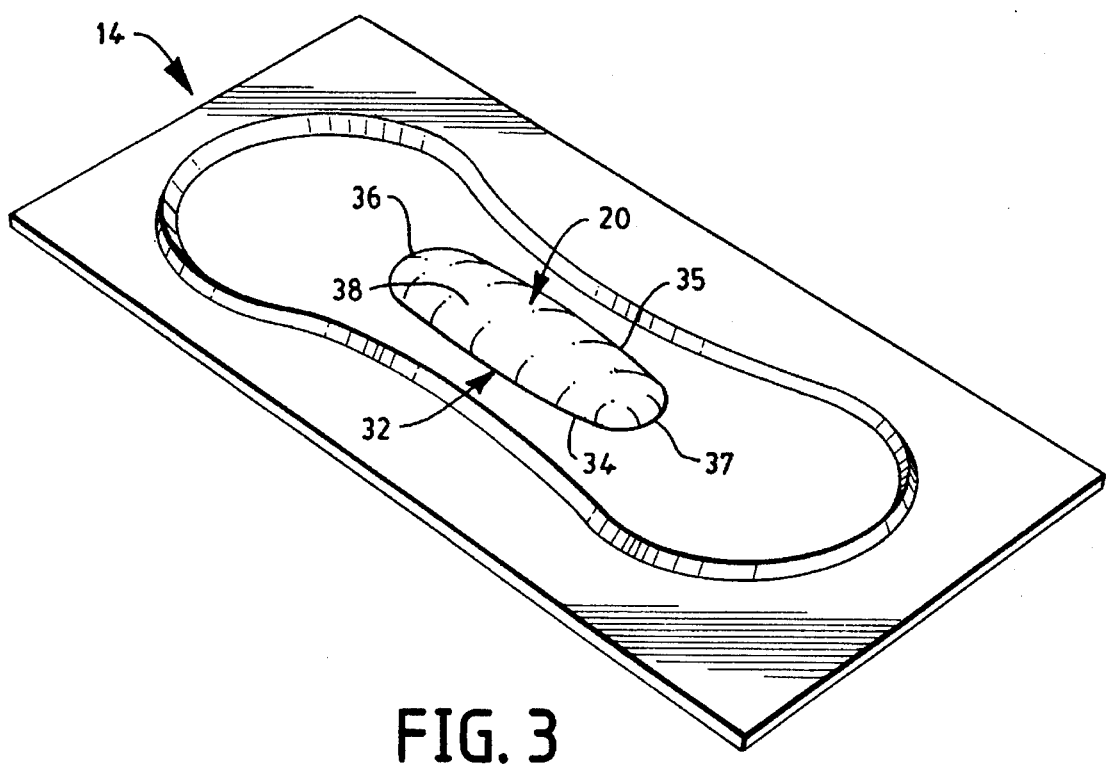
FIG. 3 is a perspective view of the preformed member illustrating the bulge medially positioned and the barrier.

Referring to FIGS. 1–3 the sanitary napkin 10 includes an optional bodyfacing, liquid-permeable cover 12, a garment-facing liquid-impermeable preformed member 14, an absorbent core 16 intermediate the cover 12 and the preformed member 14. The preformed member 14 has a barrier 18 positioned adjacent to the absorbent core 16 and a bulge 20. The sanitary napkin 10 has a pair of spaced apart longitudinal edges 22 and 23 and transverse ends 24 and 25, which collectively form the perimeter 26 of the sanitary napkin 10.

The sanitary napkin 10 is about 150 millimeters (mm) to about 300 mm long and about 50 mm to about 175 mm wide at its widest point. The sanitary napkin 10 has an hourglass configuration but can include such shapes as rectangular, oval, racetrack, dogbone and the like. The sanitary napkin 10 should have a caliper of less than about 10 mm but will preferably range from a few millimeters to about 7 mm and more preferably from about 2 mm to about 4 mm. The methodology of caliper measurement is explained in greater detail below.

As is customary in the art, the cover 12 is fluid pervious and is adapted to reside on that side of the sanitary napkin 10 to be in contact with the body of the wearer, i.e., directionally, bodyfacing. The cover 12 can be a resilient, relatively non-absorbing fluid pervious material. The cover 12 is provided for comfort and conformability and functions to direct fluid to the underlying absorbent core 16 which retains any discharged fluid. The cover 12 can be constructed of any woven or nonwoven material which is easily penetrated by body fluid contacting its surface. Preferably, the cover 12 is made of a material which allows the passage of fluid without wicking it appreciably in a horizontal plane parallel to the cover 12. Furthermore, the cover 12 should retain little or no fluid in its structure so that it provides a relatively dry surface next to the skin. Generally, the cover 12 is a single, rectangular sheet of material having a width sufficient to overlie the bodyfacing side of the absorbent core 16. The cover 12 can be constructed of bonded carded webs of polyester, polypropylene, polyethylene, nylon, or other heat-bondable fibers. Other polyolefins, such as copolymers of polypropylene and polyethylene, liner low-density polyethylene, finely perforated film webs and net material also work well. Other suitable materials are composite materials of polymer and a nonwoven fabric material. The composite sheets are generally formed by extrusion of polymer onto a web of spunbond material to form an integral sheet. This material is preferred because the outer fabric surface is not irritating to the skin of the wearer and has a cushion feel.

Another preferred material for the cover 12 is a spunbond web of polypropylene. The web can contain about 1 to 6 percent titanium dioxide pigment to give it a clean white appearance. A uniform spunbond material is desirable because it has sufficient strength, after being perforated in the longitudinal direction, to resist being torn or pulled apart during use. The most preferred polypropylene webs have a weight of between about 16 and 40 grams per square meter. Desirably, the weight is between about 20 and about 35 grams per square meter.

The liquid-permeable cover 12 can also contain a plurality of apertures (not shown) formed therein. Such apertures should be sized so fluid can pass through the cover 12 and into the absorbent core 16. The apertures can be arranged along a longitudinal central axis X—X of the sanitary napkin 10 or can be zoned or localized to the area intended to be insulted with the body fluid, if desired. The apertures are intended to increase the rate at which body fluids can penetrate down into the absorbent core 12. This helps maintain a perceivably drier surface for the cover 12 than when the apertures are not present. Therefore, while the apertures are not essential, a functional advantage is obtained by their use.

The liquid-permeable cover 12 can also be treated with a surfactant to make it more hydrophilic and, thereby, aid in the absorption of the liquid. The surfactant can include topical additions or internally applied materials like polysiloxanes.

The absorbent core 16 has a bodyfacing surface 28 that is located adjacent to the cover 12. The absorbent core 16 has an outer periphery 30 located inward from the perimeter 26 of the sanitary napkin 10. The cover 12 and the preformed member 14, in combination, will enclose the absorbent core 16. The absorbent core 16 provides a means for absorbing the menstrual fluid. The total absorbent capacity of the absorbent core 16 should be compatible with the predetermined exudate loading in the intended use of the sanitary napkin 10. Preferably, the sanitary napkin 10 is adapted to absorb fluid from a woman having a medium to heavy flow. Generally, the amount of body fluid, including menses, is greater than about 5 grams. Further, the size and shape of the absorbent core 16 can be varied. For example, the absorbent core 16 can be rectangular, oval or racetrack. Preferably, the absorbent core 16 has an hourglass configuration.

The absorbent core 16 is generally made from one or more materials that, in combination, are substantially hydrophilic, compressible, conformable and non-irritating to the wearer's skin. Acceptable materials are well known in the art and include, for example, various natural or synthetic fibers, wood pulp fibers, regenerated cellulose or cotton fibers, or a blend of pulp and other fibers, meltblown polymer, such as polyester, and polypropylene. The absorbent layers may also be comprised of other well-known materials used in absorbent articles, including multiple layers of cellulose wadding, rayon fibers, cellulose sponge, hydrophilic synthetic sponge, such as polyurethane, and the like.

The absorbent core 16 can be a composite of absorbent materials that exhibit a density gradient, from low to high, relatively speaking, in the Z-direction, as seen in FIG. 1. It has been found that by providing the absorbent core 16 with a low-to-high density gradient, a capillary action is produced that draws the fluid deeper into the absorbent core 16 and desirably, away from the cover 12.

The absorbent core 16 may contain superabsorbent particles which are effective in retaining body fluids. Superabsorbents have the ability to absorb a large amount of fluid in relation to their own weight. Typical superabsorbents used in absorbent articles, such as sanitary napkins, can absorb anywhere from 5 to 60 times their weight in body fluids.

The bulge 20 has a base 32 defined by longitudinal side portions 34 and 35 and transverse end portions 36 and 37. The bulge 20 has an apex 38 that is the upper most top surface of the bulge 20. The apex 38 preferably located along the longitudinal centerline of the bulge 20. The absorbent core 16 can blanket the bulge 20, covering the aforementioned side and end portions 34–37, respectively. However, this is not preferred because the absorbent materials can adversely affect the resiliency and body conforming characteristics of the bulge 20. It is preferred that the apex 38 extend above the bodyfacing surface 28 of the absorbent core 16. This allows the bulge 20 to comfortably reside adjacent to the labia majora of the wearer. Additionally, this arrangement enhances the movement of body fluids insulting the sanitary napkin 10 away from the wearer and toward the absorbent core 16. There is also less likelihood of fluid insulting the bulge 20 rewetting the wearer. This gives the wearer a greater feeling of dryness. Preferably, the bulge 20 extends about 1 mm to about 10 mm above the bodyfacing surface 28. The bulge 20 can be longitudinally oriented and preferably, is both longitudinally oriented and medially centered along the central longitudinal axis X—X and the transverse axis Y—Y of the sanitary napkin 10. The term "median" or "medial" is used herein to mean that transverse end portions 36 and 37 of the bulge 20 are equidistant from the transverse ends 24 and 25 of the sanitary napkin 10. Accordingly, the bulge 20 does not have to be centered relative to the longitudinal edges 22 and 23 of the sanitary napkin 10, but it is preferred that the longitudinal axis X—X of the sanitary napkin 10 coincide with the longitudinal centerline of the bulge 20.

The bulge 20 can be any shape provided that it at least contacts a portion of the labia majora of the wearer. The bulge 20 can be asymmetrically or symmetrically shaped. Nonlimiting examples of suitable configurations for the bulge 20 include oval, rectangular, square, box shaped, cylindrical having a plane passing longitudinally from one end to the other, and semi-spherical, i.e., dome shaped. The length of the bulge 20 is measured longitudinally from one transverse end portion 36 of the base 32 to the other transverse end portion 37. The length of the bulge 20 can range from between about 1.5 centimeters (cm) to the length of the absorbent core 16. Preferably it is from about 2 cm to about 12 cm, and more preferably, from about 4 cm to about 8 cm. The width is generally measured from one longitudinal side portion 34 of the base 32 to the other longitudinal side portion 35 along the transverse axis Y—Y. The width of the bulge 20 can vary from about 1 cm to about 5 cm. Preferably it is from about 1.5 cm to about 4 cm and most preferably, from about 1.5 cm to about 3 cm. The height of the bulge 20 is the vertical distance H, in the Z-direction, from the plane of the base 32 to the plane of the apex 38. The height H of the bulge 20 is from about 3 mm to about 25 mm. Preferably, it is from about 3 mm to about 20 mm and more preferably, from about 5 mm to about 15 mm. The dimensions of the bulge 20, other than the caliper, are measured using a standard ruler without any load being placed on the product.

It is to be understood that the height of the bulge 20 can be different from the caliper. The caliper typically will be used to express the thickness of the sanitary napkin 10 measured from the opposing external surfaces. For example, referring to FIG. 2, the caliper of the bulge 20 at the apex 38 would include the thickness of the preformed member 14 at the bulge 20 and the cover 12; whereas the height of the bulge 20 is the vertical distance H from the plane of the base 32 to the plane of the apex 38.

Referring to FIGS. 1–4, outboard of the base 32 is a planar region 40. The planar region 40 extends from the base 32 to the periphery 30 of the absorbent core 16. The planar region 40 is substantially flat and can have from about 15% to 100% of the absorbent capacity of the absorbent core 16 located in this region. Placing a substantial portion of the absorbent capacity of the sanitary napkin 10 in the planar region 40 draws fluids contacting the bulge 20 away from the point of insult and into the absorbent core 16. This gives the sanitary napkin 10 and in particular the area of contact with the wearer's body a dry and comfortable feel. The surrounding planar region 40 should have a caliper of less than about 10 mm but will preferably range from a few millimeters to about 7 mm and more preferably from about 2 mm to about 4 mm.

The caliper of the planar region 40 can be measured in accordance with the following procedure. All measurements are made on newly unpacked absorbent products. Each sanitary napkin 10 should be removed from its package for at least 30 minutes and handled carefully to avoid compressing, or otherwise affecting the properties thereof. Unless otherwise stated, all tests are performed at a relative humidity of 50%, 2% and a temperature of 73° F. and with any peel strip removed and the adhesive blocked using talc or corn starch.

Figure 4:
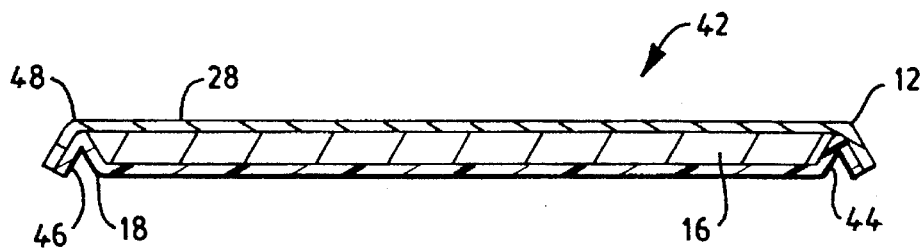
FIG. 4 is a cross-sectional view of the sanitary napkin taken along line 4—4 of FIG. 1.

To expose the planar region 40 for thickness measurement, the sanitary napkin 10 can be transversely cross-sectioned through the transverse central axis Y—Y, as seen in FIG. 1. Alternatively, transversely cross-sectioned adjacent to one of the transverse end portions 36 or 37 of the bulge 20 to expose the end area 42 or 43, as seen in FIG. 4. The sanitary napkin 10 can be cross-sectioned using any device that will not excessively compress the surrounding area, such as a knife, scissors, paper cutter, and the like. A suitable gauge for measuring the caliper is #22P-20 available from Federal Products Company of Providence, R.I. This thickness gauge typically has opposing flat circular feet each ¼" diameter, a stroke length of 1", gauge depth of 2", and 1/1000" increments on its dial. The dial meets ANSI specification #B89.1.10. The spring tension ranges from 30 gram (start of stroke) to 60 gram (fully open, end of stroke). The gauge is first zeroed. The sample is cut as described above to expose the end area 42 of the planar region 40. The samples should have as few a wrinkles as possible before testing. The feet of the gauge are spread apart and the sample is placed between them. The gauge feet are released and allowed to come together gently such that the feet rest on the opposing external surfaces of the planar region 40. The sample feet should be oriented generally parallel to the opposing surfaces so that a true thickness value for the planar region 40 is obtained. The caliper of the planar absorbent region 40 is determined by reading the dial 30 seconds after the foot comes in contact with the sample.

Referring to FIG. 4, the barrier 18 encircles the absorbent core 16 so that the barrier effectively delimits the absorbent core 16. The barrier 18 has an inner wall 44 spaced apart from an outer wall 46. The walls 44 and 46 are joined together to form an inverted "V" or inverted "U" configuration having an upper most portion 48. The inner wall 44 is positioned proximate the absorbent core 16 and the outer wall 46 is positioned distally or away from the absorbent core 16. By "encircles" it is meant that the barrier 18 substantially forms a closed loop or 360 degrees. The width and height of the barrier 18 should be sufficient to permit the barrier 18 to adapt to changes in the surface contour of the wearer and effectively intercept the migrating body fluid to prevent side leakage. Such changes are generally attributed to the variable placements of the sanitary napkin 10 in the undergarment and the general physiology differences of the individual wearer. The barrier 18 preferably should have a height so that the upper most portion 48 is at least even with the plane of the bodyfacing surface 28 of the absorbent core 16 at the periphery 28. Preferably, the upper most portion 48 will extend above the bodyfacing surface 28, and most preferably, will extend 1 mm to about 5 mm above the bodyfacing surface 38.

Since the barrier 18 will be in contact with the body of the wearer, and preferably in the thigh region, effectively forming a gasket between the wearer and the sanitary napkin 10, it is advantageous for the barrier 18 to be covered by a material that is soft and compliant, such as the cover 12. The cover 12 can be secured to the outer wall 46 of the barrier 20. The method of securing the cover 12 to the barrier 18 and if so desired the absorbent core 16, may be any suitable method that does not leave a hard, uncomfortable residue that would be annoying to the wearer. Methods for joining the various materials are well known to those skilled in the art and include the use of pressure sensitive adhesives, double-sided tape, sonic bonding, and heat sealing to name a few. Adhesives, such as hot melt adhesives can be applied in a uniform manner and as a continuous or non-continuous layer.

The preformed member 14 may be made of a high-molecular weight material which is impermeable to liquid, flexible and is capable of springing back to its original position even if deformed. A material mainly composed of cross-linked polyolefin foam, particularly cross-linked polyethylene foam may be used for the preformed member 14. Such material may have different physical characteristics and sizes. For instance, cross-linked polyethylene foam can be formed into a sheet with a thickness ranging from about 0.5 mm to about 5 mm. The strength and flexibility of the preformed member 14 will vary depending on the stiffness of the sanitary napkin 10 prior to the preformed member 14 being incorporated into the article and the use to which it is to be put. The extent of foaming ranges from about 10% to about 40% and a density of from about 0.025 grams/cubic centimeter (g/cc) to about 0.1 g/cc. Cross-linked polyolefin is light, and is capable of holding its shape. The material, however, will lose its shape-holding capability if its thickness is below 0.5 mm, and it will have poor flexibility and workability above a certain thickness. It will have poor flexibility and shape-holding capability at an increased degree of foaming. This foam may be formed by any known method. A material mainly composed of cross-linked polypropylene foam (cross-linked polyolefin) may also be used. Cross-linked material may be equally used whether the cross-linking is effected by chemical process or electronic process.

The cross-linked polyethylene foam provides a liquid-impermeable, substantially flexible preformed member 14. The preformed member 14 can have various geometries ranging from a planar or flat shape to an arcuate shape along the longitudinal axis X—X. By "arcuate" it is meant that when the preformed member 14 is placed on a flat or planar surface at least one of the end areas 42 or 43 will be spaced above the surface. The preformed member 14, when deformed, substantially returns to its original shape. The polyethylene-containing foam preformed member 14 is prepared by known thermal molding processing. For example, the sheet of polyethylene foam can be heated to its softening point. The softened material is then positioned against a forming mold and vacuum molded into the desired shape. After removing the preformed member 14 form the mold it is allowed to cool and then cut to the desired dimension. The preferred formulation for forming the ethylene-containing polymer foam material is identified as Volara Type E which is a cross-linked ethylene/vinyl acetate copolymer foam. Also suitable for the present invention is a material identified as Volara Type A which is a cross-linked polyethylene foam. The products are manufactured and sold by Voltek, Inc., Lawrence, Mass. Preferably, the formulation is prepared in sheet form and has a thickness of about 1 mm to about 5 mm, preferably the sheet is about 1 mm to about 3 mm in thickness. The sheet is subjected to thermal molding at a temperature between about 220° F. to about 300° F. to form the foam preformed member 14.

An advantage of the sanitary napkin 10 utilizing a bulge 20 of the above-described characteristics and incorporating a barrier 18 is that the bulge 20 can be less dense, resilient, and more comfortable to the wearer. This provides for a sanitary napkin 10 that is less intrusive to the wearer than sanitary napkins previously known or used that incorporate a hump, an extension or an elevated surface.

Another advantage of the present invention is that utilization of the absorbent material is increased by impeding the flow of any body fluid toward the outer perimeter 26. This gives the absorbent core 16 additional time to absorb the body fluid.

Figure 5:
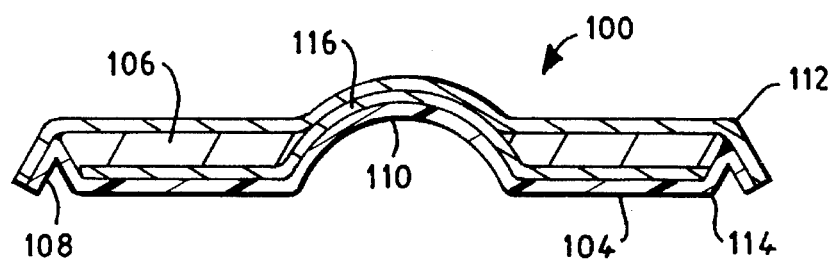
FIG. 5 is a cross-sectional view of another embodiment of this invention taken along line Y—Y illustrating a wicking layer residing over the bulge.

Referring to FIG. 5, a cross-sectional view of a sanitary napkin 100 is illustrated showing an alternative embodiment of this invention. The sanitary napkin 100 includes a bodyfacing, liquid-permeable cover 102, a garment-facing, liquid-impermeable preformed member 104 and an absorbent core 106 positioned between the cover 102 and the preformed member 104. The preformed member 104 has a barrier 108 and a bulge 110. The absorbent core 106 has a bodyfacing surface 112 disposed toward the cover 102 and a garment-facing surface 114 disposed toward the preformed member 104. The sanitary napkin 100 also includes a wicking layer 116 positioned adjacent to the absorbent core 106. A function of the wicking layer 116 is to distribute the body fluid across a surface of the absorbent core 106, thereby increasing the efficacy of the absorbent core 106. The wicking layer 116 is preferably positioned between the absorbent core 106 and the preformed member 104 and, more preferably, the wicking layer 116 extends above the bodyfacing surface 112 and most preferably, can cover the bulge 110 of the preformed member 104. This configuration advantageously draws fluids contacting the bulge 110 to the garment-facing surface 114 of the absorbent core 106 and away from the cover 102 to give a drier surface and enhanced absorbent utilization. The wicking layer 116 should be sized so that it can effectively transport liquids contacting its surface to the absorbent core 106. Generally this is from a few millimeters to about the entire surface lying inside the barrier 108.

The wicking layer 116 can be constructed from any material having sufficient capillary activity, or other means, to attract and transport body fluid. The wicking layer 116 may include more than one material having these characteristics. The wicking layer 116 can be comprised of a fibrous material having little absorption ability. Suitable materials include blends of polyester and rayon that have minimum fluid retaining character. Other materials may be airformed or carded webs of polyester, rayon, or polypropylene. A preferred material for the wicking layer 116 is a meltblown polypropylene layer having a thickness of about 0.6 mm, a weight of about 60 grams per square meter. Such a material is available from the Kimberly-Clark Corporation having offices at 401 North Lake Street, Neenah, Wis.

Figure 6:
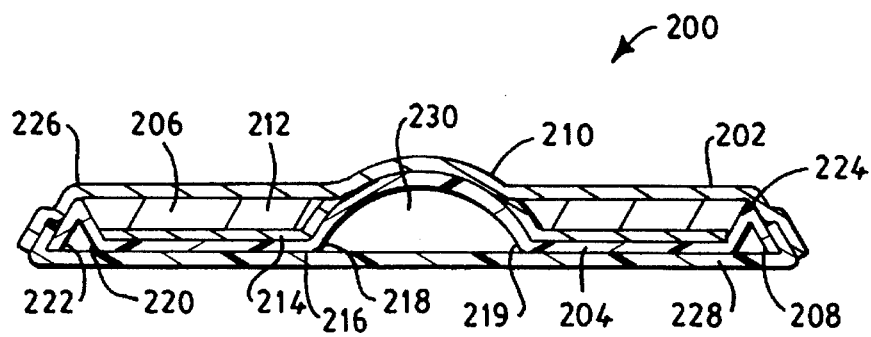
FIG. 6 is a cross-sectional view of another embodiment of this invention illustrating a pocket formed by the bulge of the preformed member and a liquid-impermeable baffle.

Referring to FIG. 6, a cross-sectional view of a sanitary napkin 200 is illustrated showing an alternative embodiment of this invention. The sanitary napkin 200 includes a bodyfacing, liquid-permeable cover 202, a garment-facing, liquid-impermeable preformed member 204, and an absorbent core 206 positioned between the cover 202 and the preformed member 204. The preformed member 204 includes a barrier 208 and a bulge 210. The absorbent core 206 has a bodyfacing surface 212 disposed toward the cover 202. The sanitary napkin 200 includes an optional wicking layer 214 similar to that described above positioned adjacent to the absorbent core 206. The bulge 210 has a base 216 defined by longitudinal side portions 218 and 219, and transverse end portions (not shown). The barrier 208 has an inner wall 220 spaced apart from an outer wall 222. The inner wall 220 is positioned adjacent to the absorbent core and the outer wall 222 is positioned distally or away from the absorbent core 206. The walls 220 and 222 are joined together to form an inverted "V" or inverted "U" configuration having an upper most portion 224. The inner wall 220 of the barrier 208 encircles the absorbent core 206 to define an outer periphery 226. The barrier 208 should have a height so that the upper most portion 224 is even with the plane of the bodyfacing surface 212 of the absorbent core 206. Preferably, the upper most portion 224 will extend above the bodyfacing surface 212 and most preferably, will extend 1 mm to about 5 mm above the bodyfacing surface 212.

The sanitary napkin 200 further includes a liquid-impermeable baffle 228 secured to at least a portion of the garment-facing surface of the preformed member 204. The baffle 228 is at least dimensionally sized so that it can be secured to the base 216 of the bulge 210 and preferably is large enough to be secured to the outer wall 222 of the barrier 208. The bulge 210 and the baffle 228 cooperate to form a pocket 230. The pocket 230 is advantageous in keeping the bulge 210 properly positioned against the labia majora of the wearer. The pocket 230 provides a cushion feel and adds resilience to the bulge 210.

The baffle 228 can permit the passage of air or vapor out of the sanitary napkin 200 while blocking the passage of body fluids. The baffle 228 may be any desired material that is liquid-impermeable. A good material is a micro-embossed, polymeric film, such as polyethylene or polypropylene having a thickness of about 0.001 to about 0.005 of an inch (0.025 to 0.13 millimeters). Bi-component films can also be used as well as woven and nonwoven fabrics which have been treated to render them liquid-impermeable.

Figure 7:
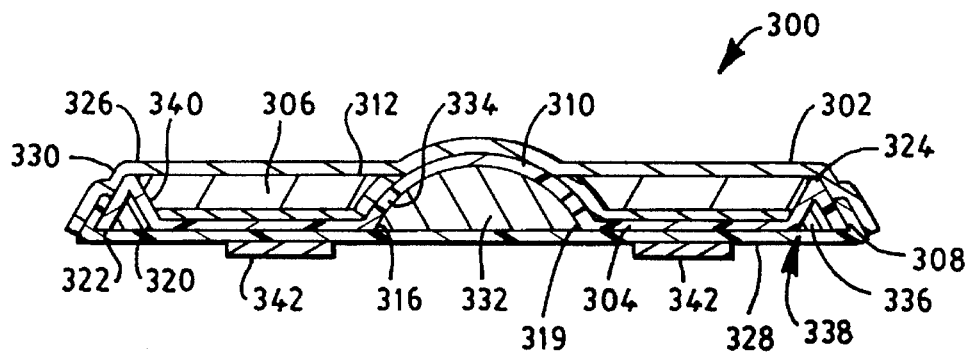
FIG. 7 is a cross-sectional view of another embodiment of this invention illustrating a plurality of absorbent cores.

Referring to FIG. 7, a cross-sectional view of a sanitary napkin 300 is illustrated showing an alternative embodiment of this invention. The sanitary napkin 300 includes a bodyfacing, liquid-permeable cover 302, a garment-facing, liquid-impermeable preformed member 304, and a first absorbent core 306 positioned between the cover 302 and the preformed member 304. The preformed member 304 includes a barrier 308 and a bulge 310. The absorbent core 306 has a bodyfacing surface 312 disposed toward the cover 302. The sanitary napkin 300 includes an optional wicking layer 314 similar to that described above positioned adjacent to the first absorbent core 306. The bulge 310 has a base 316 defined by longitudinal side portions 318 and 319, and transverse end portions (not shown). The barrier 308 has an inner wall 320 spaced apart from an outer wall 322. The inner wall 320 is positioned adjacent to the first absorbent core 306 and the outer wall 322 is positioned distally or away from the first absorbent core 306. The walls 320 and 322 are joined together to form an inverted "V" or inverted "U" configuration having an upper most portion 324. The inner wall 320 of the barrier 308 encircles the first absorbent core 306 to define an outer periphery 326. The barrier 308 should have a height similar to that described above.

The sanitary napkin 300 further includes a liquid-impermeable baffle 328. The baffle 328 enwraps the garment-facing surface of the preformed member 304 and is secured to the base 316 of the bulge 310 and to the outer wall 322. Preferably the baffle 328 is secured to an outer surface 330 of the barrier 308. A second absorbent core 332 is positioned between the bulge 310 and baffle 328. One or more first apertures 334 in the bulge 310 permit body fluid contacting the bulge 310 to be absorbed into the second absorbent core 332. The first apertures 334 can reside above the bodyfacing surface 312, below, or any position therebetween. A third absorbent core 336 is positioned in a recessed area 338 formed between the inner wall 320, the spaced apart outer wall 322 and the baffle 328. One or more second apertures 340 in the inner wall 320 permit body fluid contacting the inner wall 320 to be absorbed into the third absorbent core 336. The second aperture(s) 340 can reside above the bodyfacing surface 312, below, or any position therebetween. Preferably, the second aperture(s) 340 reside below the bodyfacing surface 312. This permits liquid communication between the third absorbent core 336 and the first absorbent core 306 via one or more second aperture(s) 340.

Providing the sanitary napkin 300 with second and third absorbent cores 332 and 336 total absorbent capacity of the sanitary napkin 300 is increased without substantially adding bulk. The second absorbent core 332 and third absorbent core 336 become a liquid holding compartments for any sudden gushes of body fluid, further enhancing absorbent capacity utilization.

Furthermore, because of the flexibility of the preformed member 304, the second and third absorbent cores 332 and 336 add a degree of rigidity in specific areas without compromising comfort and the adaptability of the sanitary napkin 300 to conform to the body of the wearer.

The sanitary napkin 300 of the present invention can be provided with strips of adhesive 342 applied to the garment-facing side of the baffle 328. The adhesive strips 342 are positioned longitudinally but avoiding the area superposed by the bulge 310 so that the adhesive will not interfere with the performance of the bulge 310. Typically, the adhesive is pressure sensitive adhesive capable of securing the sanitary napkin 300 to the crotch portion of an undergarment, yet permitting removal of the panty liner when soiled. The adhesive strips 342 generally are covered by a protective release liner (not shown) such as a Kraft paper that is silicone coated.

In use, the wearer removes the release liner and attaches the sanitary napkin 300 to the inside surface of the undergarment. The adhesive strips 342 allow the sanitary napkin 300 to remain in position to receive discharged liquids.

Several alternative embodiments of sanitary napkins which can be provided with a medial bulge and barrier are shown and described in U.S. Pat. No. 5,219,341 issued to Serbiak et al. on Jun. 15, 1993, U.S. patent application Ser. No. 08/263,178 filed on Jun. 21, 1994 in the name of Couture-Dorschner et al. and U.S. patent application Ser. No. 08/058,249 filed on May 12, 1993 in the name of Hirt et al. The disclosures of all patents and disclosed herein are hereby incorporated by reference herein and made a part hereof.

While the particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the spirit and scope of this invention.

We claim:

1. An absorbent article having an outer perimeter and adapted to be worn adjacent to a wearer's body, said absorbent article comprising:
   a) a liquid-impermeable preformed member; and
   b) an absorbent core secured to and superposed over a portion of said preformed member, said absorbent core having a bodyfacing surface and said preformed member having a bulge with an apex extending above said bodyfacing surface, said preformed member further having barrier means for intercepting body fluid migrating toward said outer perimeter, said barrier means encircling said absorbent core.

2. The absorbent article of claim 1 having a central longitudinal axis and said bulge is longitudinally oriented relative to said axis.

3. The absorbent article of claim 2 wherein said bulge is medially positioned along said central longitudinal axis.

4. The absorbent article of claim 1 wherein said absorbent core has an outer periphery and said barrier means has a height at least equal to said bodyfacing surface of said absorbent core at said outer periphery.

5. The absorbent article of claim 2 wherein said preformed member has a predetermined arcuate shape along said longitudinal axis.

6. The absorbent article of claim 1 wherein said preformed member is a flexible, thermal formable polyolefin.

7. The absorbent article of claim 6 wherein said polyolefin is a cross-linked foam.

8. The absorbent article of claim 7 wherein said polyolefin foam is polyethylene foam.

9. The absorbent article of claim 7 wherein said polyolefin foam is polypropylene foam.

10. The absorbent article of claim 7 wherein said preformed member has a caliper between about 0.5 mm to about 3 mm.

11. The absorbent article of claim 1 further comprising:
    c) a liquid-permeable cover positioned adjacent to said bodyfacing surface; and
    d) a wicking layer located between said absorbent core and said preformed member.

12. The absorbent article of claim 11 wherein said wicking layer extends above said bodyfacing surface of said absorbent core.

13. An absorbent article having an outer perimeter and adapted to be worn adjacent to a wearer's body, said absorbent article comprising:
    a) a liquid-permeable cover;
    b) a liquid-impermeable preformed member having a garment-facing surface;
    c) an absorbent core having a predetermined thickness of less than about 5 mm and positioned between said cover and said preformed member, said absorbent core having a bodyfacing surface and said preformed member having a bulge with an apex extending above said bodyfacing surface, said preformed member further having barrier means for intercepting body fluid migrating toward said outer perimeter, said barrier means encircling said absorbent core; and
    d) a liquid-impermeable baffle secured to a portion of said garment-facing surface of said preformed member wherein a pocket is formed between said bulge and said baffle.

14. The absorbent article of claim 13 having a central longitudinal axis and said bulge is longitudinally oriented relative to said axis.

15. The absorbent article of claim 14 wherein said bulge is medially positioned along said central longitudinal axis.

16. The absorbent article of claim 13 wherein said absorbent core has an outer periphery and said barrier means has a height at least equal to said bodyfacing surface at said outer periphery.

17. The absorbent article of claim 13 wherein said preformed member is a flexible thermal formable cross-linked polyolefin foam.

18. The absorbent article of claim 13 wherein said bulge has a base and said baffle is secured to said base.

19. The absorbent article of claim 17 wherein said polyolefin foam is polyethylene foam having a caliper of about 0.5 mm to about 3 mm.

20. The absorbent article of claim 13 wherein said barrier means has an inner wall and a spaced apart outer wall joined together with an upper most portion, said upper most portion extending above said bodyfacing surface, said baffle extending across said garment-facing surface and being secured to said outer wall.

21. An absorbent article having an outer perimeter and adapted to be worn adjacent to a wearer's body, said absorbent article comprising:
    a) a liquid-permeable cover;
    b) a liquid-impermeable preformed member;
    c) a first absorbent core positioned between said cover and said preformed member, said first absorbent core having a bodyfacing surface and said preformed member having a bulge with an apex extending above said bodyfacing surface, said preformed member further having barrier means for intercepting body fluid migrating toward said outer perimeter, said barrier means having an inner wall and a distally spaced outer wall joined together;

d) a liquid-impermeable baffle secured to a portion of said garment-facing surface of said preformed member; and e) a second absorbent core positioned between said bulge and said baffle, said bulge having an aperture for liquid absorption into said second absorbent core.

22. The absorbent article of claim 21 further comprising a third absorbent core positioned between said inner wall, said spaced apart outer wall and said baffle, said inner wall having a second aperture for liquid absorption into said third absorbent core.

23. The absorbent article of claim 22 wherein said second aperture is positioned below said bodyfacing surface of said first absorbent core.

* * * * *